United States Patent
Salmon-Legagneur et al.

(10) Patent No.: US 11,857,324 B2
(45) Date of Patent: Jan. 2, 2024

(54) SYSTEM FOR MONITORING THE OPERATIONAL STATUS OF AN AIRCRAFT CREW, AND ASSOCIATED METHOD

(71) Applicant: DASSAULT AVIATION, Paris (FR)

(72) Inventors: François Salmon-Legagneur, Saint Cloud (FR); Valentin Ligier, Saint-Cloud (FR); Cyril Saint Requier, Saint-Cloud (FR)

(73) Assignee: DASSAULT AVIATION, Paris (FR)

( * ) Notice: Subject to any disclaimer, the term of this patent is extended or adjusted under 35 U.S.C. 154(b) by 0 days.

(21) Appl. No.: 17/676,128

(22) Filed: Feb. 19, 2022

(65) Prior Publication Data

US 2022/0265187 A1 Aug. 25, 2022

(30) Foreign Application Priority Data

Feb. 22, 2021 (FR) ...................................... 21 01673

(51) Int. Cl.
*G08B 23/00* (2006.01)
*A61B 5/18* (2006.01)
*A61B 5/00* (2006.01)

(52) U.S. Cl.
CPC ................ *A61B 5/18* (2013.01); *A61B 5/742* (2013.01); *A61B 5/746* (2013.01); *A61B 5/7475* (2013.01)

(58) Field of Classification Search
CPC ........... A61B 5/18; A61B 5/742; A61B 5/746; A61B 5/7475
USPC ...................................................... 340/573.1
See application file for complete search history.

(56) References Cited

U.S. PATENT DOCUMENTS

| | | | |
|---|---|---|---|
| 8,493,239 B2 | 7/2013 | Dehais et al. | |
| 8,725,318 B1* | 5/2014 | McCusker | G06F 3/1423 701/3 |
| 9,637,133 B1* | 5/2017 | McCusker | A61B 5/18 |
| 9,919,712 B1* | 3/2018 | Doyen | A61B 5/14542 |
| 10,135,927 B1* | 11/2018 | Barber | H04L 67/12 |
| 10,426,393 B2 | 10/2019 | Bosworth et al. | |

(Continued)

FOREIGN PATENT DOCUMENTS

| | | |
|---|---|---|
| CA | 2141627 | 8/1995 |
| EP | 2257469 A1 | 12/2010 |

(Continued)

OTHER PUBLICATIONS

Search Report for priority application FR 210673.

(Continued)

*Primary Examiner* — Naomi J Small
(74) *Attorney, Agent, or Firm* — Davidson, Davidson & Kappel, LLC (57) ABSTRACT

A system for monitoring the operational status of an aircraft crew includes a unit for determining at least one pilot state based on first monitoring data of a high design assurance level and second monitoring data of a lower design assurance level. The determination unit includes a first evaluation module capable of obtaining a high-level pilot state from the first data, regardless of the second data; a second evaluation module capable of determining a low-level pilot state, from at least the second data; and a consolidation module for determining a consolidated pilot state. The consolidated pilot state is obtained as a function of the high-level pilot state and the low-level pilot state.

17 Claims, 8 Drawing Sheets

(56) References Cited

U.S. PATENT DOCUMENTS

| | | |
|---|---|---|
| 2006/0220883 A1 | 10/2006 | Matos |
| 2009/0273487 A1 | 11/2009 | Ferro et al. |
| 2011/0018739 A1 | 1/2011 | Dehais |
| 2011/0040156 A1 | 2/2011 | Vij |
| 2012/0116610 A1 | 5/2012 | Righi et al. |
| 2014/0316660 A1 | 10/2014 | Le et al. |
| 2018/0105039 A1 | 4/2018 | Yeomans |
| 2019/0267025 A1 | 8/2019 | Clement et al. |
| 2019/0369615 A1 | 12/2019 | Martinez Jara et al. |
| 2020/0153810 A1* | 5/2020 | Schwindt ............ G06F 11/3664 |
| 2022/0073189 A1* | 3/2022 | Farjon ................. G05D 1/0061 |

FOREIGN PATENT DOCUMENTS

| | | |
|---|---|---|
| EP | 2341491 A2 | 7/2011 |
| EP | 2635941 A1 | 9/2013 |
| EP | 2868274 A1 | 5/2014 |
| EP | 3154038 A1 | 4/2017 |
| KR | 20160036968 A | 4/2016 |
| WO | WO2009125091 A1 | 10/2009 |

OTHER PUBLICATIONS

Liu Jing et al: Cognitive Pilot-Aircraft Interface for Single-Pilot Operations, Knowledge-Based Systems, vol. 112, Sep. 6, 2016, pp. 37-53.

* cited by examiner

SYSTEM FOR MONITORING THE OPERATIONAL STATUS OF AN AIRCRAFT CREW, AND ASSOCIATED METHOD

BACKGROUND

The present disclosure relates to a system for monitoring the operational state of an aircraft crew, comprising:
- a first interface for receiving first crew monitoring data, the first monitoring data having a high design assurance level;
- a second interface for receiving second crew monitoring data, the second monitoring data having a lower design assurance level than the first monitoring data;
- a unit for determining at least one pilot state based on the first high design assurance level monitoring data received from the first receiving interface, and the second lower design assurance level monitoring data received from the second receiving interface.

Such a system is intended in particular to be integrated into the avionics of an aircraft to monitor the operational state of at least one crew member of the aircraft, in particular to determine degraded states that may disrupt or endanger the operation of the aircraft. The system monitors each pilot on station independently and simultaneously, or alternatively, only one of the pilots on station.

Examples of degraded states are absence of the crew member from the cockpit, total or partial incapacitation of the crew member, drowsiness, inattention, overwork and/or overcommitment to a task.

The operational state of each pilot, i.e. their ability to operate the aircraft reliably and consciously, is an important parameter in ensuring safe flight. Indeed, inattentional failures of individual pilots due to fatigue or stress, and in the worst case, total or partial incapacitation of the pilot, or their absence from the cockpit, can lead to substantial risks in the conduct of the flight, or even to accidents.

Generally, each pilot on station ensures the operational state of the other pilot on station, monitoring that pilot's reactions, and checking their actions.

However, in some cases, it may be useful to complement the monitoring action carried out by each pilot on the other pilot with automatic means in order to objectively detect degraded states of a crew member.

To this end, systems exist to monitor the operational state of an aircrew. For example, U.S. Ser. No. 10/426,393 describes a system for monitoring the health of a pilot, using a plurality of sensors that measure physiological parameters of the pilot, and/or track the actions of the pilot.

Current monitoring systems are based on sensors whose reliability does not necessarily meet the high standards required in the field of aviation.

In addition, these monitoring systems sometimes use artificial intelligence modules that are capable in some cases of detecting degraded states by learning. However, these systems can provide erroneous results in other unpredictable cases, causing false alarms about the degraded state of the monitored pilot.

This type of monitoring system is therefore generally an aid, or at least an additional safety net for pilots, but its reliability does not correspond to what is required in the field of aviation, in particular to obtain certification from the competent authorities.

SUMMARY

It is therefore an aim of the present disclosure to provide a system for monitoring the operational state of an aircraft crew, which allows for both highly reliable and responsive monitoring of the state of at least one crew member, that system being preferably capable of meeting certification requirements.

To this end, the present disclosure has as its subject matter a system of the aforementioned type, characterised in that the determination unit comprises, for the or each monitored pilot state:
- a first high-level evaluation module, adapted to implement a first deterministic algorithm to obtain a high-level pilot state from the first high design assurance level monitoring data, regardless of the second lower design assurance level monitoring data;
- a second lower-level evaluation module, suitable for determining a low-level pilot state, from at least the second lower design assurance level monitoring data;
- a consolidation module for determining a consolidated pilot state, wherein the consolidated pilot state is obtained in an active configuration of the second lower-level evaluation module as a function of the high-level pilot state and the low-level pilot state, and in an inactive configuration of the second lower-level evaluation module as a function of the high-level pilot state, without taking the low-level pilot state into account.

The design assurance level ("DAL") is usually determined for a particular system producing data by operational safety studies and by a risk analysis examining the consequences of a system fault or failure condition.

The possible design assurance levels are for example defined in ARP4754. For example, they are designated by letters, as follows:
- Level A: A fault in the system or subsystem under consideration may cause a catastrophic problem—Flight safety or landing compromised—Aircraft crash (e.g. Level A requires a fault or failure occurrence rate of $10^{-9}$/flight hours or less);
- Level B: A fault in the system or subsystem under consideration may cause a hazardous problem resulting in serious damage or even death to some occupants (e.g. level B requires a fault or failure occurrence rate of $10^{-7}$/flight hours or less);
- Level C: A fault in the system or subsystem under consideration may cause a major problem resulting in a malfunction of the aircraft's vital equipment (e.g. level C requires a fault or failure occurrence rate of $10^{-5}$/flight hours or less);
- Level D: A fault in the system or subsystem under consideration may cause a minor problem with no effect on flight safety (e.g. level D requires a fault or failure occurrence rate of $10^{-3}$/flight hours or less);
- Level E: A fault in the system or subsystem under investigation may cause a problem that has no effect on flight safety.

The terms "high design assurance level" and "lower design assurance level" are understood in a relative way depending on the design assurance level of the system generating the data. For example, if levels A, B, or C are considered in a particular implementation of the present disclosure to be "high design assurance levels", then levels D and E are considered to be "lower design assurance levels".

The system according to the present disclosure may comprise one or more of the following features, taken alone or in any combination that is technically possible:
- the consolidated pilot state determined by the consolidation module is suitable for changing from a normal state to at least one degraded state, the high-level pilot state being suitable for changing from a normal high-level state to at least one degraded high-level state, the low-level pilot state being suitable for changing from a normal low-level state to a degraded low-level state, the consolidation module being adapted to establish a degraded pilot state when the first high-level evaluation module determines a high-level degraded pilot state and/or when the second lower-level module determines a low-level degraded pilot state;

the first high-level evaluation module comprises a first finite-state machine implementing the first deterministic algorithm;

the second lower-level evaluation module is suitable for implementing a second algorithm, preferably a second deterministic algorithm;

the second lower-level evaluation module comprises a second finite-state machine implementing the second algorithm;

the first reception interface is suitable for receiving, together with each first data item, a validity level associated with the first data item, the second reception interface being suitable for receiving, together with each second data item, a validity level associated with the second data item, the high-level evaluation module and the low-level evaluation module being able to take into account the validity levels of the first data items and of the second data items in order to determine the high-level and low-level pilot states and/or to determine a validity level associated with the pilot state in question;

the second lower-level evaluation module is adapted to receive first high design assurance level monitoring data from the first receiving interface, the second lower-level evaluation module being adapted to obtain the low-level pilot state based on second lower-level design assurance monitoring data obtained from the second interface and on first high design assurance level monitoring data obtained from the first interface;

the first high-level evaluation module is adapted to calculate a high-level confidence level associated with the or each determined high-level pilot state, the second low-level evaluation module is adapted to calculate a low-level confidence level associated with the determined low-level pilot state, the consolidation module is adapted to calculate a consolidated confidence level associated with the consolidated pilot state, based on the high-level confidence level and the low-level confidence level;

the consolidated pilot state is selected from a state of presence at his/her work station, a state of aircraft operation ability, in particular incapacitation and/or sleep, a state of alertness, in particular drowsiness, distraction and/or inattention, a state of work overload, a state of mental overload, a state of stress, a state of present situation awareness, a state of task engagement, a state of physical activity level, and/or a state of pilot activity consistency and mission-relevance;

the determination unit comprises a command for deactivating the lower-level evaluation module, accessible to a crew member, suitable for switching the lower-level evaluation module from the active configuration to the inactive configuration;

the command to deactivate the low-level evaluation module is a dedicated physical command, a virtual command on a screen, and/or a command in a window of a display of the monitoring system;

the first receiving interface and/or the second receiving interface is adapted to receive data from an avionics system, and/or data from the crew member's interaction with a human/machine interface of the avionics system;

the first receiving interface and/or the second receiving interface is adapted to obtain sensor data for monitoring the state of the crew member;

the sensors for monitoring crew member conditions comprise a sensor for detecting the presence of a crew member on the seat, an optical detection sensor with a field of view facing a seat of the crew member, in particular a camera operating in the visible, near-infrared, or thermal spectrum, and/or a 2D and/or 3D time-of-flight camera, and/or at least one sensor for detecting physiological parameters, in particular an ECG sensor, a breathing detection sensor, an EEG sensor, an FNIR sensor, a sensor for measuring physiological data housed in a connected watch, a connected bracelet or in a connected garment;

the system comprises a display, and a display manager on the display, adapted to generate and display on the display a state monitoring window illustrative of the or each consolidated pilot state determined by the determination unit;

the system comprises an information generator, in particular a notification or message generator, and/or an alarm generator, capable of generating at least one item of information, in particular a notification or message, and/or at least one alarm when a consolidated pilot state determined by the determination unit is in a degraded state;

the system comprises a display, and a display manager on the display, adapted to generate and display on the display at least one window for monitoring the operating state and selective deactivation of the or each crewmember state monitoring sensor, the setting of the detection sensitivity level of each crewmember state monitoring sensor, the setting of the information and/or alarm level, and/or the silencing or turning off of the monitoring system;

for the or each monitored pilot state, the first high-level evaluation module determines a high-level pilot state associated with the monitored pilot state, the second low-level evaluation module determines a low-level pilot state associated with the monitored pilot state, the monitored pilot state being obtained from the consolidated pilot state obtained by the consolidation module or being the consolidated pilot state obtained by the consolidation module.

The present disclosure also relates to a method of monitoring the operational state of an aircrew, implemented in a monitoring system, comprising the following steps:

receiving, via a first receiving interface of the monitoring system, first crew monitoring data, the first monitoring data having a high design assurance level;

receiving, via a second receiving interface of the monitoring system, second monitoring data with a lower design assurance level than the first monitoring data;

determining, via a determination unit of the monitoring system, at least one pilot state based on the first high design assurance monitoring data received from the first receiving interface, and the second lower design assurance monitoring data received from the second receiving interface, the determination comprising, for the or each monitored pilot state:

implementation of a deterministic algorithm by a first high-level evaluation module of the determination unit to obtain a high-level pilot state from the first high design assurance level monitoring data, regardless of the second lower-level design assurance monitoring data;

determination of a low-level pilot state by a second lower-level evaluation module of the determination unit from at least the second lower-level design assurance monitoring data;

determination of a consolidated pilot state by a consolidation module of the determination unit, wherein the consolidated pilot state is obtained in an active configuration of the second lower-level evaluation module as a function of the high-level pilot state and the low-level pilot state, and is obtained in an inactive configuration of the second lower-level evaluation module as a function of the high-level pilot state, without taking into account a low-level pilot state.

The method according to the present disclosure may comprise the following feature:

when the high-level pilot state changes from a normal high-level state to a degraded high-level state, and/or when the low-level pilot state corresponding to the high-level pilot state changes from a normal low-level state to a degraded low-level state, the consolidation module determines that the consolidated pilot state has changed from a normal state to a degraded state.

BRIEF DESCRIPTION OF THE DRAWINGS

The present disclosure will be better understood upon reading the following description, given only as an example, and with reference to the attached drawings, in which.

DETAILED DESCRIPTION

Figure 1:
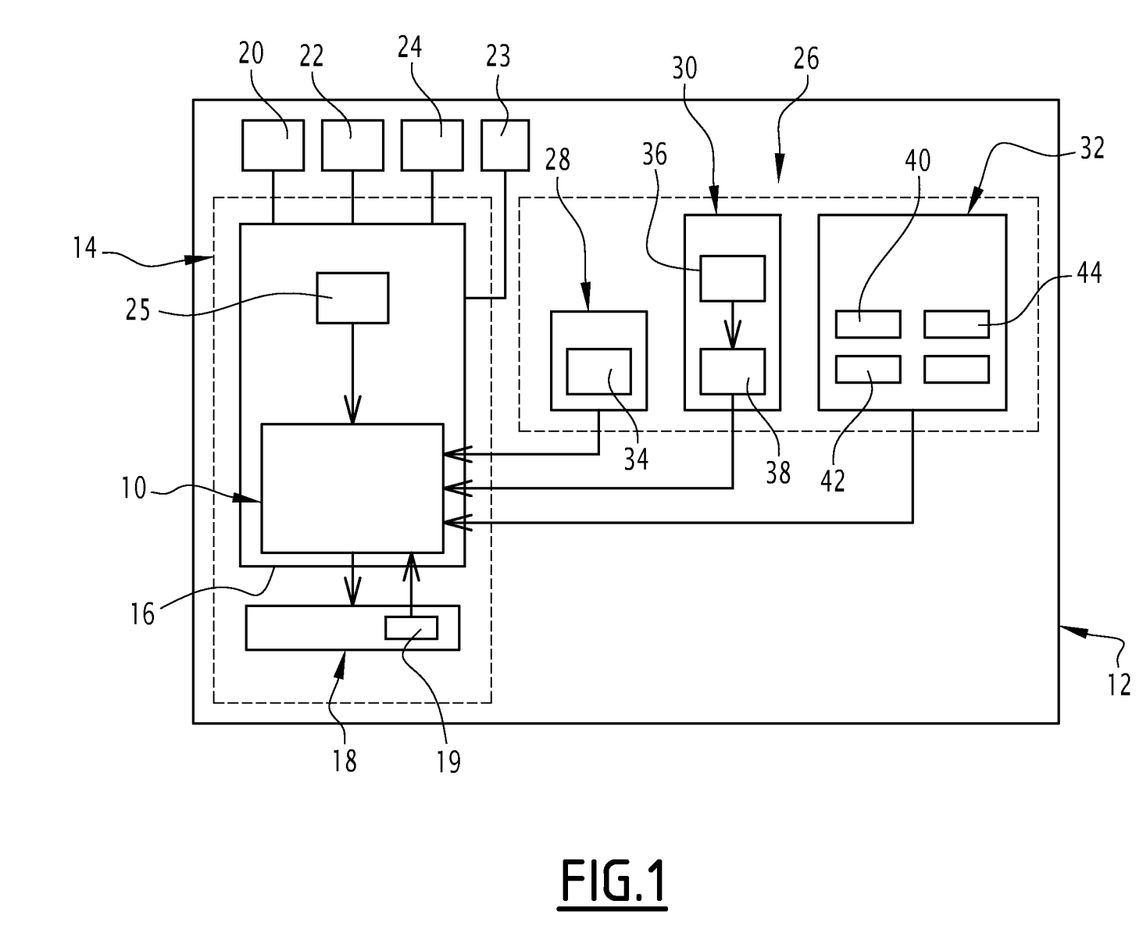
FIG. 1 is a block diagram illustrating a system for monitoring the operational state of an aircrew according to the present disclosure, integrated into the avionics of an aircraft.
Figure 2:
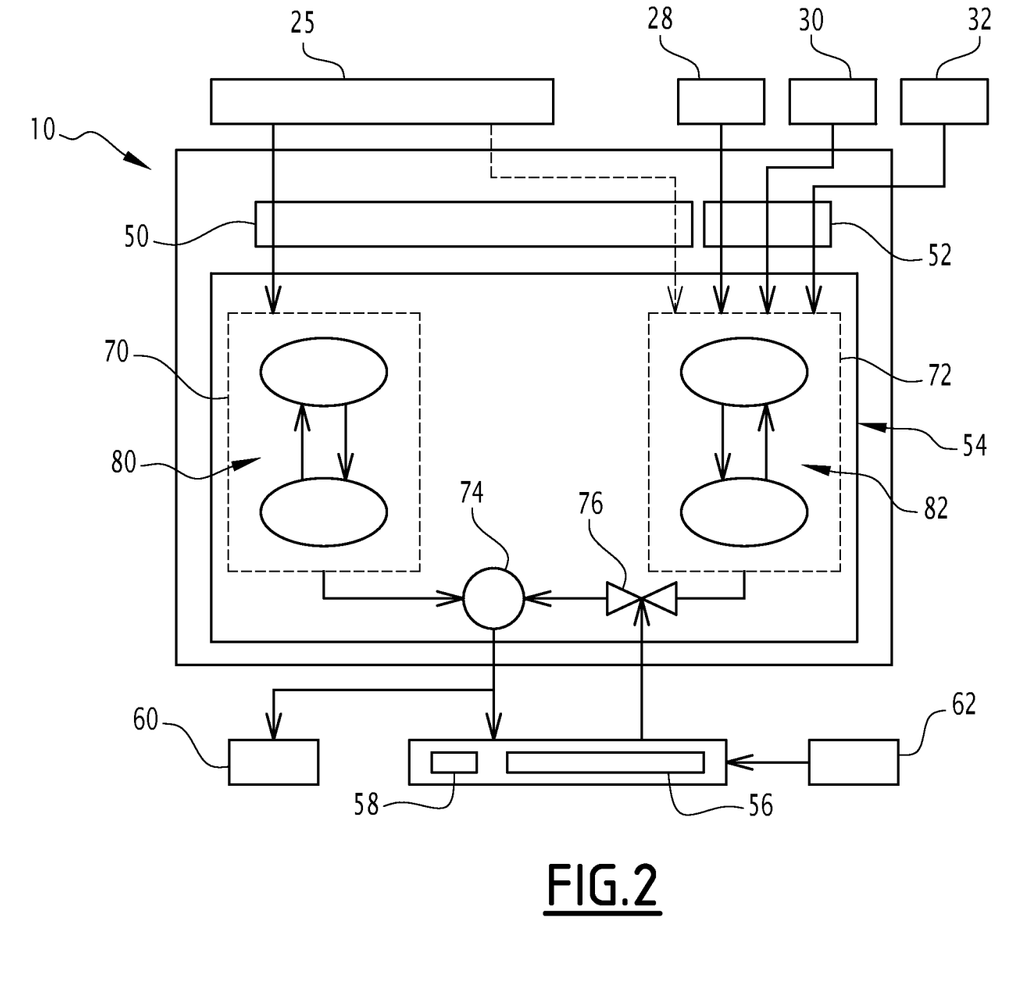
FIG. 2 is a block diagram illustrating in more detail the pilot state determination unit of the monitoring system of FIG. 1, with high-level and lower-level evaluation modules.

A first system 10 for monitoring the operational state of an aircraft 12 crew is schematically depicted in FIGS. 1 and 2.

The system 10 is intended to be connected to or integrated with a central avionics system 14 comprising a central avionics unit 16, at least one display unit 18 located in a control interface of the aircraft 12 and at least one human-machine interface 19 enabling the crew to interact with the central avionics unit 14, in particular to command the functional systems of the aircraft 12.

The control interface of the aircraft 12 is for example located in the aircraft 12 itself (in the cockpit), or in a remote control room of the aircraft 12 (in a ground station).

In particular, the central avionics unit 16 is connected to aircraft 12 equipment, a component of the aircraft's functional systems.

The functional systems of the aircraft 12 include, for example, systems 20 for measuring the state of the aircraft, systems 22 for external communication, systems 24 for activating aircraft commands, and systems 23 for navigation and operational mission management.

The measurement systems 20 comprise, for example, components comprising sensors for measuring parameters external to the aircraft, such as temperature, pressure or speed, sensors for measuring parameters internal to the aircraft and its various functional systems and positioning sensors, such as GPS sensors, inertial units, and/or an altimeter.

The external communication systems 22 include, for example, components comprising radio, VOR/LOC, ADS, DME, ILS, radar systems, and/or satellite communication systems.

The control systems 24 include components comprising actuators for operating aircraft controls, such as flaps, control surfaces, pumps, mechanical, electrical and/or hydraulic systems, and software actuators for configuring the avionics states of the aircraft.

The navigation and operational mission management systems 23 include, for example, a flight management system, and possibly a mission task management system. These systems are capable of identifying the flight phase and assisting pilots in navigating the aircraft along a trajectory, and in managing the tasks associated with navigation. They are suitable for producing data for use by the monitoring system 10 such as identification of the current flight phase, aircraft altitude, time of day, etc.

The various systems 20 to 24 are connected to the central avionics unit 14, for example digitally, by at least one data bus 25 running on an internal network within the aircraft 12.

The data bus 25 is able to carry in particular the data required by the system 10 to operate.

These data are, for example, avionics data, in particular control activation data on the interface 19, Cursor Control Device (CCD) data for controlling the interface 19, or other user interaction data with the interface 19, in particular on the aircraft's displays 18.

When at least one crew member performs actions interacting with the central avionics system 14, for example operates commands, or interacts with pointing and cursor designating devices, or with touch screens on the aircraft, first high design assurance level data is generated. The initial high design assurance level data thus generated usually identifies which crew member is performing these interaction actions.

The monitoring system 10 is also connected to a crew-monitoring sensor system 26, which is not integrated into the central avionics system 14. Here, the sensors of the crew monitoring sensor system 26 produce data, which may be high design assurance level data and/or lower-level design assurance data, and which may also be carried by the data bus 25.

As mentioned above, the data design assurance level is for example defined by ARP4754.

In the example shown in FIG. 1, the sensor system 26 advantageously includes a seat presence detection sensor 28, arranged on a seat intended to receive a crew member in the aircraft control interface, a camera system 30 and/or at least one additional sensor 32.

The seat presence sensor 28 comprises for example a pressure gauge 34, which is able to detect that a member of the crew is exerting pressure on the seat cushion and/or the seat back.

The camera system 30 comprises at least one camera 36, and an analysis device 38 of the images produced by the camera 36, for determining presence and movement data of a crew member present in the aircraft control interface, as well as a direction of vision of the crew member and advantageously other physiological and cognitive parameters associated with the crew member (such as drowsiness, distraction, etc.)

The camera 36 is for example a camera operating in the visible, near-infrared, thermal, and/or time-of-flight spectrum, in 2D and/or 3D.

The additional sensors 32 comprise for example a sensor 40 for measuring the heart rate of a crew member, in particular an electrocardiography (ECG) sensor, sensors 42 for measuring mental activity of the crew member, in particular functional near-infrared (FNIR) sensors or electroencephalography (EEG) sensors. The additional sensors 32 advantageously include wrist sensors, such as connected watches 44 or other miscellaneous sensors that can be interfaced with the monitoring system 10 within the crew-monitoring sensor system 26.

With reference to FIG. 2, the crew operational state monitoring system 10 comprises a first interface 50 for exclusively receiving first crew monitoring data having a high design assurance level, and a second interface 52 for receiving second crew monitoring data having a lower level of design assurance.

The crew operational state monitoring system 10 further comprises a unit 54 for determining at least one pilot state based on the first monitoring data received from the first receiving interface 50 and the second monitoring data received from the second interface 52. It further comprises a display 56 and a display manager 58 on the display 56, suitable for displaying at least one crew monitoring window.

The crew operational state monitoring system 10 advantageously further comprises an information and/or alarm generator 60, and at least one human/machine interface 62 to allow the crew to interact with the crew operational state monitoring system 10.

The pilot state determination unit 54 is suitable for determining a pilot state, or preferably for determining several pilot states in parallel.

The pilot state is for example a state of presence at his/her work station, a state of aircraft operability, in particular incapacitation and/or sleep, a state of alertness, in particular drowsiness, distraction, or inattention, a state of work overload, a state of mental overload, a state of stress, a state of present situation awareness, a state of task engagement, a state of physical activity level, and/or a state of pilot activity consistency and mission-relevance.

The pilot state determination unit 54 comprises, for example, a processor, and at least one memory for receiving software modules suitable for execution by the processor to perform functions.

Alternatively, the computer 54 comprises programmable logic components or dedicated integrated circuits to perform the functions of the modules described below.

With reference to FIG. 2, the pilot state determination unit 54 comprises, for the or each monitored pilot state, a first evaluation module 70 of the first high design assurance level data, suitable for implementing a deterministic algorithm to obtain a high-level pilot state, from the first high design assurance level data only, without taking into account the second lower-level design assurance data.

The pilot state determination unit 54 further comprises, for the or each monitored pilot state, a second lower level evaluation module 72, suitable for determining a low-level pilot state, in particular from the second lower level design assurance data.

The pilot state determination unit 54 also comprises, for the or each monitored pilot state, a consolidation module 74, which is adapted to determine, in an active configuration, a consolidated pilot state on the basis of the high-level pilot state and the low-level pilot state. It further comprises a command 76 suitable for switching the consolidation module 74 to an inactive configuration of the second evaluation module 72 so that the consolidation module 74 determines the pilot state based on the high-level pilot state only.

The or each pilot state determined by the consolidation module 74 is a state selected from a normal state and at least one degraded state.

The degraded state is determined for example from a state of absence of the pilot from their work station, a state of incapacitation or sleep of the pilot preventing the pilot from operating the aircraft, a state of light or heavy drowsiness, a state of loss of alertness, a state of overwork and/or a state of overcommitment to a task. Further degraded states can be defined depending on the sensors present in the sensor system 26.

For each pilot state, a normal state corresponds to the degraded state. The normal state is, for example, a state of presence of the pilot at their station, a state of ability or alertness of the pilot to operate the aircraft, a state of alertness, a state of normal workload and/or a state of normal commitment to a task.

The states of absence, incapacity and/or sleep, in which the pilot is unable to report via the interface 19 after a request, are likely to generate information, for example messages or notifications, and possibly even alerts by the information and/or alarm generator 60.

By way of example, the absence condition may be detected from the first high-level data, in the absence of activity on the avionics controls by a crew member for a predefined period of time (e.g. 5 minutes) and cumulatively, when no pilot reaction is observed in response to a prompt window issued at a display 18 of the avionics system 14.

The absence state may also be detected by the absence of pressure on the seat exerted by the crew member for a predefined period of time (e.g. 30 seconds), detected by the pressure gauge 34 of the presence detection sensor 28, or by the absence of facial recognition performed by the image analysis device 38 coupled to the camera 36 of the camera system sensor 30, for a predefined period of time (e.g. 1 minute).

The incapacitated and/or sleeping state may be detected by the absence of pilot activity on the avionics controls for a predefined period of time (e.g. 5 minutes), and cumulatively by the absence of pilot response to a prompting window after a predefined period of time (e.g. 30 seconds).

Generally, incapacitation and/or sleep are not detectable at the pressure gauge 34 of the seat position sensor 28, which does detect the presence of the crew member. On the other hand, incapacitation and/or sleep are also detectable by the image analysis device 38 linked to the camera 36 of the camera system 30 in the absence of pilot movement, or by the detected posture of the pilot's body.

The state of drowsiness is detected, for example, by measuring the eye activity of the seated pilot with the camera 36 and the image analysis device 38.

The state of inattention is measured using the camera system 30, by measuring the position of the user's gaze, in particular if this position is away from the positions the user should be looking at in relation to the interfaces or cockpit, for example because they are consulting a mobile phone or tablet. Furthermore, this is corroborated with a lack of pilot activity on the controls, and possibly a lack of pilot response to a prompt.

Degraded states of absence and inactivity (incapacitation and/or sleep), are intended to be detected at least by the high level evaluation module 70. They are able to be detected in parallel by the lower level evaluation module 72.

In this example, degraded states of drowsiness and/or inattention are likely to be detected primarily by the lower level assessment module 72.

The first high level evaluation module 70 is connected to the first interface 50, to exclusively receive first high design assurance level monitoring data.

It comprises at least a first state machine 80, which is able to implement a deterministic algorithm based on the first high design assurance level monitoring data. The first state machine 80 is intended to determine the high-level pilot state, between a normal state and a degraded state as defined above.

Preferably, the first high-level evaluation module 70 presents a state machine 80 for each pilot state to be determined, between the normal pilot state and the degraded pilot state. It therefore comprises at least one state machine 80 for the absence state and at least one state machine 80 for the incapacity and/or sleep state.

The first evaluation module 70 is thus adapted, for the or each pilot state monitored by the determination unit 54, to obtain a high-level pilot state, chosen between a normal high-level pilot state and a degraded high-level pilot state.

The state machine 80 implements a deterministic algorithm, i.e. an algorithm that, in response to a set of initial monitoring data, always gives the same result.

Figure 3:
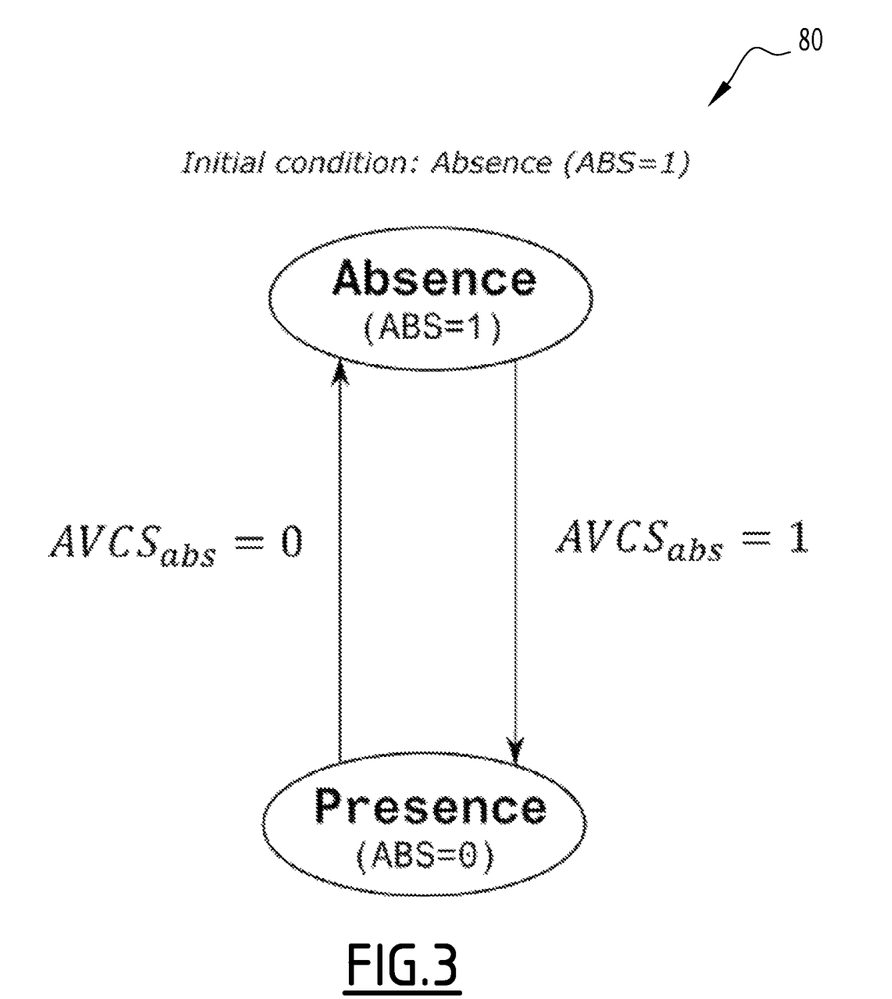
FIG. 3 illustrates an example of a finite-state machine used by the high level assessment module to determine an absent crew member state, using high level design reliability monitoring data.

An example of a state machine 80 for determining an absence state is shown in FIG. 3. The state machine 80 is adapted to determine an absence state or a presence state of the pilot in the control interface in the form of a Boolean flag here referred to as ABS. By default, the detected condition is an initial condition of absence ("initial condition: Absence (ABS=1)".

The state machine 80 is adapted to retrieve first high-level data from the interface 50 to determine a pilot detection Boolean flag $AVCS_{abs}$. The indicator has a value of 1 when, for example, the initial monitoring data indicates pilot interaction actions with the central avionics system 14 in the recent past.

The presence indicator is elaborated within the pilot state determination unit 54 from the set of data received through the interface 50, these data can only vary upon action by the pilot; they thus form an indicator of presence and human activity in the cockpit.

In this case, the transition condition being true, the absence state changes to a zero value and the pilot is detected as present. The high-level pilot state is then a normal high-level pilot state.

On the contrary, if the pilot detection Boolean flag $AVCS_{abs}$ is zero, i.e. the pilot has not acted on the controls for a predefined time, the state machine 80 returns to the absence state, which corresponds to a high-level degraded state.

In this example, the second lower level evaluation module 72 is adapted to receive second lower level design assurance monitoring data from the second interface 52, and advantageously also first high design assurance level monitoring data from the first interface 50.

The second evaluation module 72 is further adapted to determine the functional status of the sensors of the sensor system 26, and to eliminate data from sensors of the sensor system 26 that are non-functional. It is suitable for determining a low-level pilot state only on the basis of the sensors of the monitoring sensor system 26 that are operational.

The second lower level evaluation module 72 here comprises a second deterministic state machine 82 associated with each first state machine 80.

The second state machine 82 is adapted to implement a deterministic algorithm based on the second monitoring data received from the second interface 52, and possibly first monitoring data received from the first interface 50.

Figure 4:
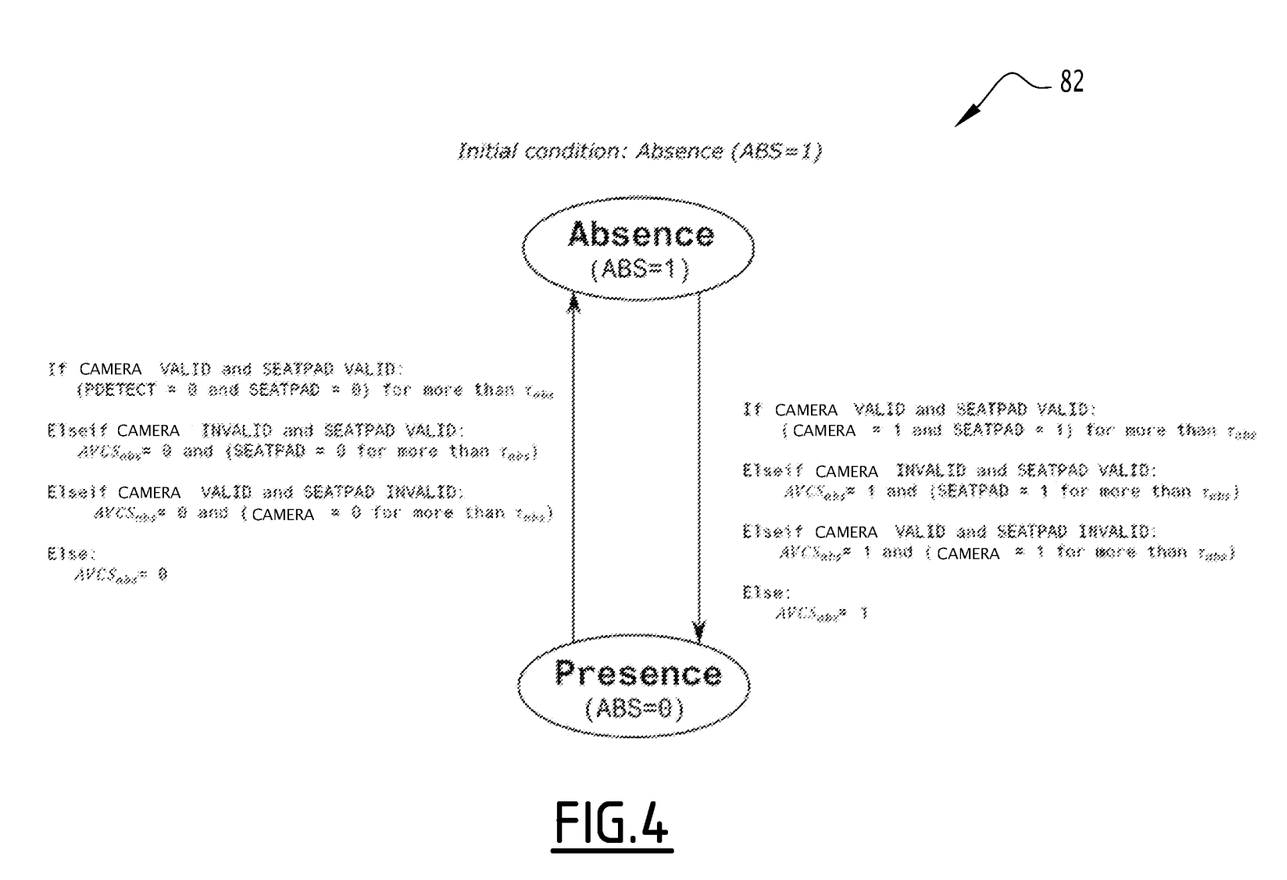
FIG. 4 shows a finite-state machine used by the low level assessment module to determine the absence of a crew member from their seat using lower-level design reliability monitoring data.

In the example shown in FIG. 4, the second state machine 82 is suitable for determining a low-level pilot state for the or each pilot state determined by the determination unit 54, which corresponds to the high-level pilot state determined by the first state machine 80 of FIG. 3.

It is suitable, for example, for determining an absence or presence state of the pilot in the control interface in the form of a Boolean flag here referred to as ABS. By default, the detected condition is an initial condition of absence ("initial condition: Absence (ABS=1)".

In this example, the second machine 82 uses second lower level monitoring data to obtain a Boolean flag SEATPAD from the pressure gauge 34 and a Boolean flag CAMERA from the analysis device 38 of images produced by the camera 36. It also uses the pilot detection Boolean flag $AVCS_{abs}$ obtained from the first high-level monitoring data.

Starting from an absence state ABS=1, if the second monitoring data from each sensor is declared valid and if the Boolean flag SEATPAD and the Boolean flag CAMERA simultaneously indicate that the pilot is present on the seat (value equal to 1 in FIG. 4) for more than a given fixed duration $\tau_{abs}$ (e.g. 5 seconds), then the normal presence state is obtained (ABS=0).

This is also the case if the Boolean flag SEATPAD alone indicates that the pilot is present on the seat (value equal to 1 in FIG. 4) for more than a given time $\tau_{abs}$, the camera data being invalid, and if the pilot detection Boolean flag $AVCS_{abs}$ indicates a pilot presence. This is also the case if the camera-related Boolean flag CAMERA alone indicates that the pilot is present on the seat (value equal to 1 in FIG. 4) for more than a given time $\tau_{abs}$, the seat data being invalid, and if the pilot detection Boolean flag $AVCS_{abs}$ indicates a pilot presence.

This is also the case if the pilot detection Boolean flag $AVCS_{abs}$ alone indicates a pilot presence when both the seat and camera sensors are declared invalid.

Similar conditions allow a degraded state of absence to be detected from the normal state of presence.

The result given by the second state machine 82 is therefore suitable for switching between a normal low-level pilot state and at least one degraded low-level pilot state, and for providing this data to the consolidation module 74.

The consolidation module 74 is adapted to consolidate the high-level and low-level pilot states produced by the first high-level evaluation module 70 and the second lower-level evaluation module 72 respectively to produce the consolidated pilot state.

The consolidation module 74 is adapted to apply consolidation logic between the high-level pilot state received from the first evaluation module 70 and the low-level pilot state received from the second evaluation module 72, in the activation configuration of the second lower level evaluation module 72.

The logic is, for example, an "OR" type logic. Thus, if at least one of the high-level or low-level pilot states is a high-level degraded state or a low-level degraded state respectively, then the consolidated pilot state is switched to the degraded state.

Instead, when the first evaluation module 70 and the second evaluation module 72 each determine a normal state, then the consolidated pilot state produced by the crew operational state monitoring system 10 is a normal pilot state.

Thus, with an architecture of the above type, which provides for segregation of monitoring data according to their design assurance level, between a high level and a lower level, each evaluation module 70, 72 takes as input the interfaces 50, 52 of a level adapted to the pilot state it is to generate, and has its own state machines 80, 82 to each determine a proper pilot state.

The first high-level evaluation module 70 guarantees a high design assurance level of the resulting pilot state, since it uses exclusively high design assurance level data as input, with a deterministic algorithm. This ensures that, in the event of a certification of the monitoring module 10, the main degraded states, in particular the absence state and the incapacitated and/or sleep state, are always detected.

However, the performance of the first state machine 80 is more limited, especially in terms of detection time and/or the type of states detected.

The second lower-level evaluation module 72 is designed to ensure operational efficiency of the system by speeding up and improving the detection scope and by integrating lower-level data, thus enriching the possible states that can be detected.

The combination of the states produced by the two modules 70, 72, within the consolidation module 74, covers the objectives that the monitoring system 10 has to fulfil, namely alerting the crew in case of incapacitation, sleep or absence of the pilot, but also operational efficiency.

Preferably, the first reception interface 50 receives, together with each first data item, a validity level associated with the first data item, which corresponds to a (possibly Boolean) quantification of the validity of the first data item, depending, for example, on faults or failures of the system(s) producing and transmitting the first data item.

Similarly, the second reception interface 52 receives, together with each second data item, a validity level associated with the second data item, which corresponds to a (possibly Boolean) quantification of the validity of the second data item, depending, for example, on faults or failures of the system or systems producing and transmitting the second data item.

In this case, the high-level evaluation module 70 is adapted to calculate a high-level validity level associated with the or each determined high-level pilot state, depending on the validity level of the first data used.

The low-level evaluation module 72 is adapted to calculate a low-level validity level associated with the determined low-level pilot state, depending on the validity level of the second data and possibly the first data used.

The consolidation module 74 is adapted to calculate a consolidated validity level of the consolidated pilot state, based on the high and low validity levels respectively, for example by taking the maximum, the average, or a weighting of the high and low validity levels respectively.

Advantageously, the algorithms implemented by the high-level and low-level evaluation modules 70, 72 are able to take into account the levels of validity of the first data and the second data, in order to adapt the logic for determining the high and low-level pilot states. This makes them robust to the loss of sensors or input data.

Advantageously, the high-level evaluation module 70 is adapted to calculate a high-level confidence level associated with the or each determined high-level pilot state. The low-level evaluation module 72 is adapted to calculate a low-level confidence level associated with the determined low-level pilot state.

Each confidence level is obtained for example from a table and/or a calculation algorithm.

The consolidation module 74 is adapted to calculate a consolidated confidence level on the basis of the high and low confidence levels respectively, for example by taking the maximum, the average, or a weighting of the high and low confidence levels respectively.

The switch 76 is adapted to be controlled from the human machine interface 62 to switch the consolidation module 74 between the configuration of activating the second lower level evaluation module 72 and the configuration of inactivating the second lower-level evaluation module 72.

In the activation configuration, the pilot state is determined from the high-level and low-level pilot states by the consolidation module 74, whereas in the deactivated configuration, only the high-level pilot states are considered by the consolidation module 74 to determine the or each pilot state.

The presence of the switch 76 makes the system 10 more reliable. When all the sensors are operating, the system 10 uses the data from all the sensors (including the low-level design assurance data), which expands the functional scope of the system 10 and is more responsive than systems producing the high design assurance level data, which are more reliable. If the sensors producing the lower level of design assurance data start to interfere with the system 10 due to their lower design assurance level, the crew can manually switch them off, refocusing the system 10 only on the high design assurance level data. Although the system 10 is then more limited in function and responsiveness, it remains safe and reliable, consistent with the certification requirements. As will be described below, the need to switch from one configuration to another is detectable by the pilot, for example by looking at the display 56.

The display manager 58 comprises, for example, a processor, and at least one memory for receiving software modules that can be executed by the processor to perform functions.

Figure 5:
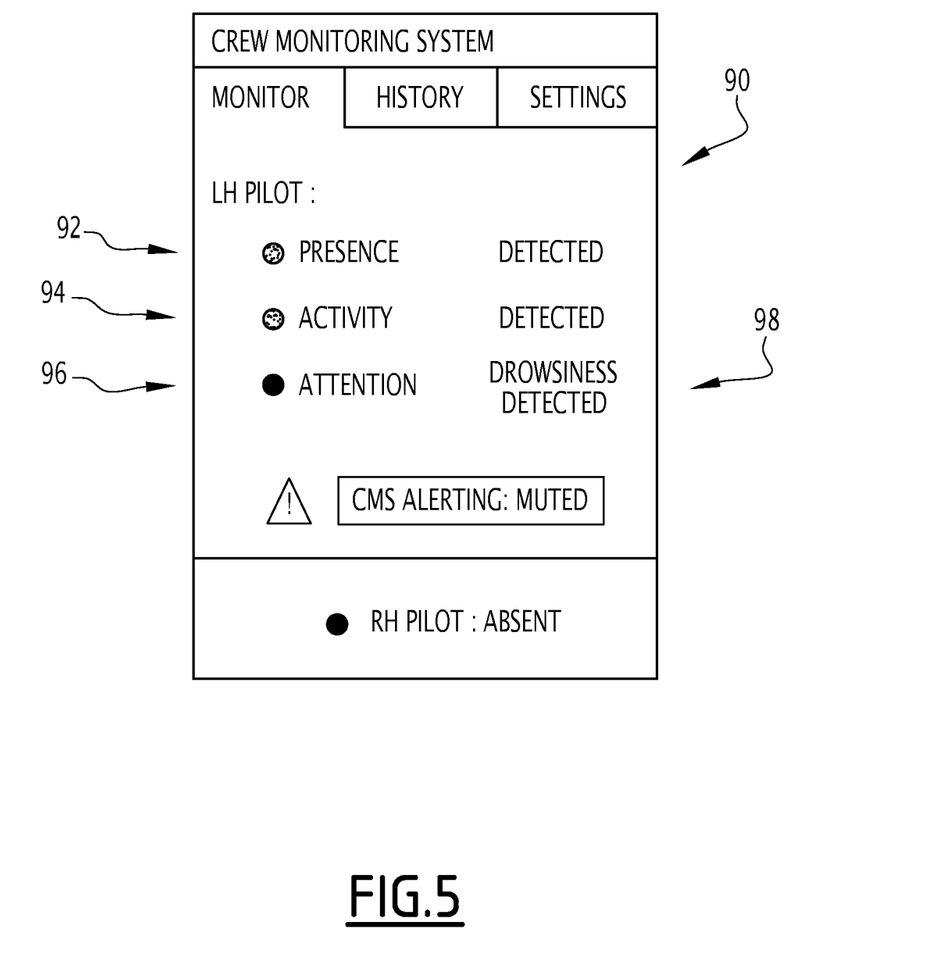
FIGS. 5 to 7 represent windows illustrative of the presentation interface, in particular of the pilot state(s) monitored by the system of FIG. 1, of the history of the pilot states, and of the command to deactivate the low-level evaluation module.

It is suitable for recovering the pilot state determined by the consolidation module of the determination unit 54, in particular a normal state and/or a degraded state of absence, incapacity and/or sleep, drowsiness or inattention. It is adapted to generate and display on the display 56 at least a first pilot state monitoring window 90, an example of which is shown in FIG. 5.

The monitoring window 90 comprises for example a first indicator 92 indicating the presence of the pilot ("DETECTED" meaning that the pilot is detected), a second indicator 94 indicating whether pilot activity is observed, resulting from the absence of incapacitation and/or sleep, and a third indicator 96 indicating the level of pilot alertness, in particular by means of a message 98 which makes it possible to determine whether drowsiness ("DROWSINESS") or inattention is detected.

Figure 6:
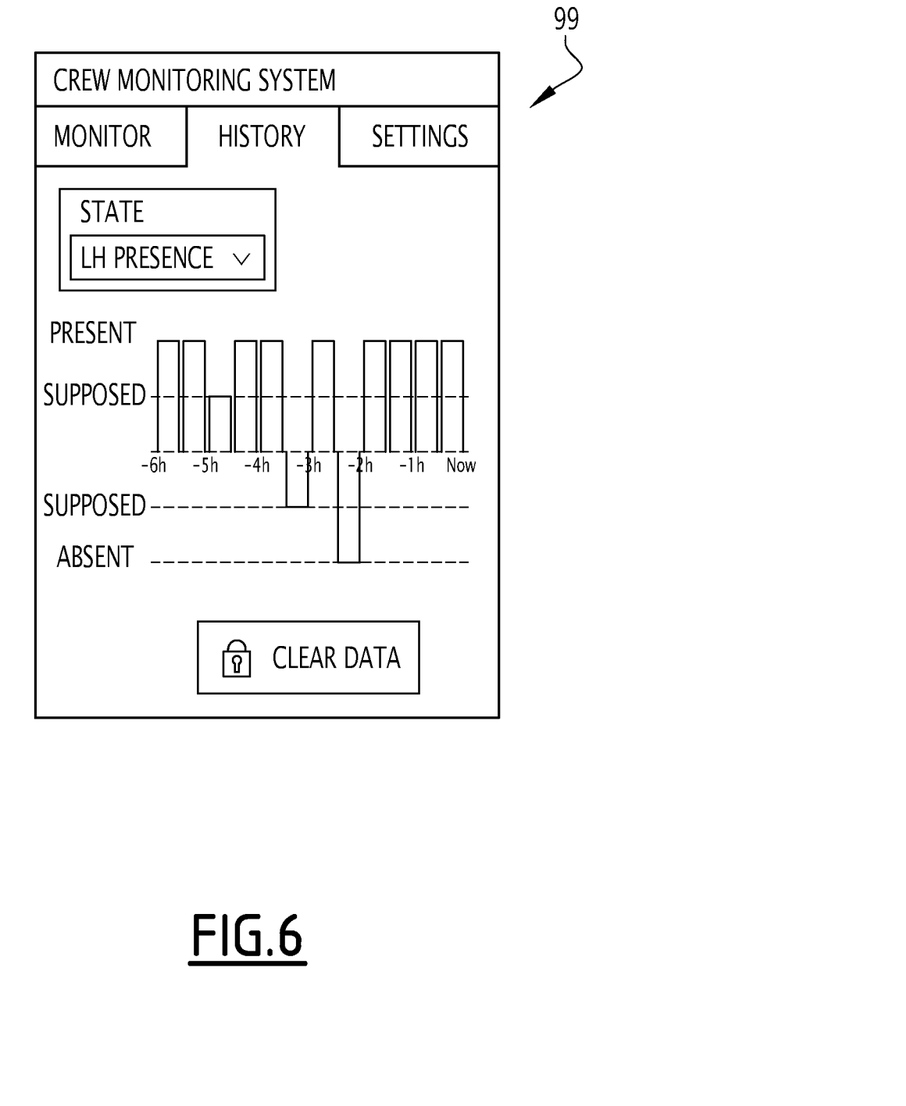

The display manager 58 is further adapted to advantageously generate a second window 99 to retrieve the history of each of the pilot states over time. For example, in FIG. 6, the pilot's seat presence history ("HISTORY") is displayed as a histogram showing the pilot's presence ("PRESENT"), supposed presence ("SUPPOSED"), supposed absence, and absence ("ABSENT"), with the level of certainty derived from the confidence level associated with the consolidated state from the consolidation module 74.

Figure 7:
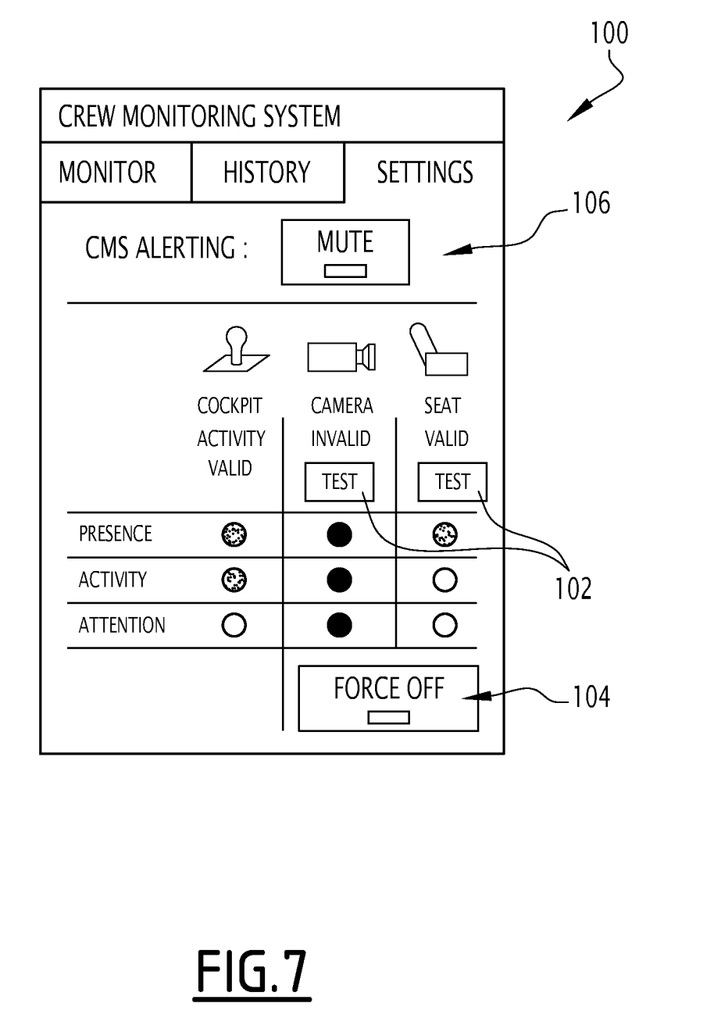

The display manager 58 is further adapted to display a window 100 for monitoring the operational state of a crew 10, visible in FIG. 7.

The window 100 comprises buttons 102 for testing the individual sensors 28, 30 of the sensor system 26, a control system 104 of the command 76 for deactivating the second lower level evaluation module 72, in case of observed malfunction of the sensors 28, 30, and optionally a button 106 for silencing the information and/or alarm generators 60.

Figure 8:
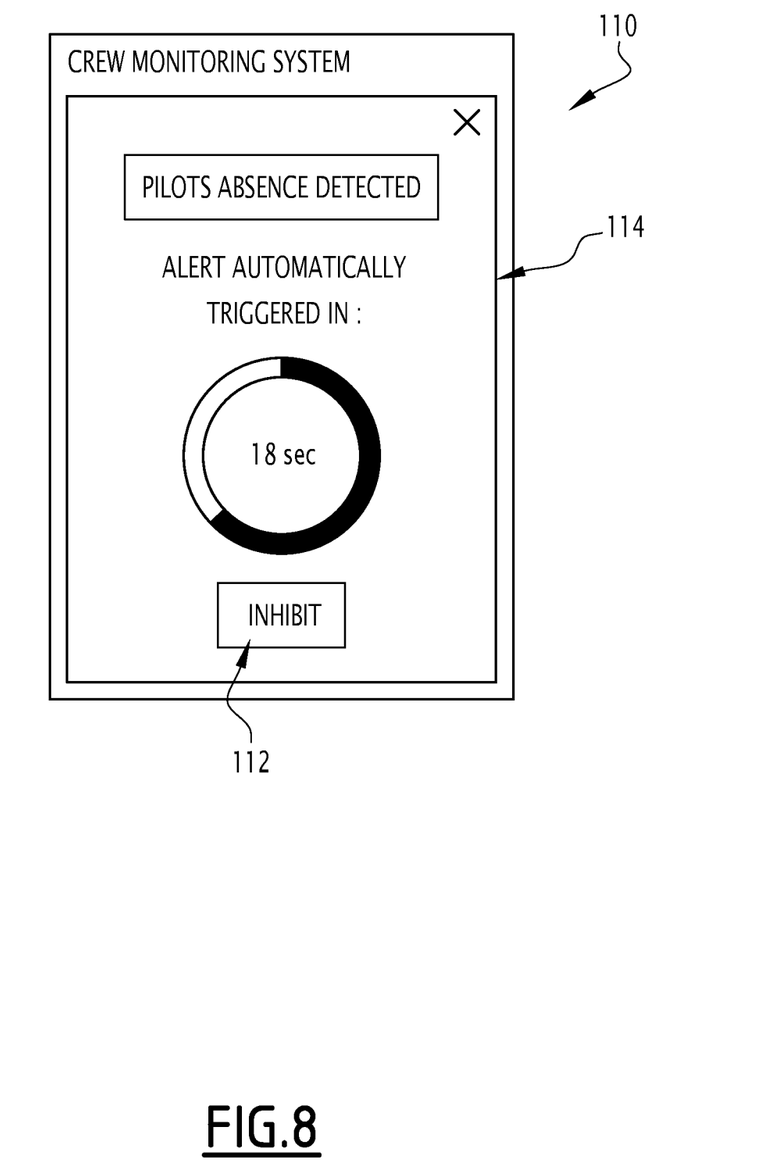
FIG. 8 illustrates an alert window that may be displayed when the monitoring system detects that the pilot is not in the cockpit.

With reference to FIG. 8, the display manager 58 is further adapted to display, in case of detection of a degraded pilot state, a pilot prompting window 110 to which the pilot must respond to confirm or deny the assumed degraded state detected by the system. This window includes an acknowledgement button 112, and a counter 114 which indicates the time remaining before the information and/or alarm generator 60 generates an alarm.

In case the pilot state is an absence, incapacity and/or sleep state, the information and/or alarm generator 60 is adapted to issue an item of information, e.g. a notification or a message or even an alarm in the control interface to the second pilot or another crew member. This alarm is for example a visual and/or audible and/or vibratory alarm. These alarms are always generated when a state of absence, incapacity and/or sleep is detected.

In addition, in the event of drowsiness or inattention, a visual, audible, or vibratory alarm is generated for the pilot concerned.

The operation of the crew operational state monitoring system 10 according to the present disclosure will now be described.

The system 10 is intended to operate preferably during the entire flight.

Once the crew operational state monitoring system 10 is activated, the first interface 50 for receiving first high design assurance level data continuously receives first monitoring data from, for example, the avionics CPU 16 over the data bus 25. This initial monitoring data reflects, among other things, pilot activity on the avionics controls and provides a high design assurance level.

Similarly, the sensors 28, 30 of the monitoring sensor system 26 are activated to detect the presence of a pilot in their seat by means of the pressure gauge 34, and/or to film the pilot, by means of the camera system 30, the data from the camera 36 being continuously analysed by the image analysis device 38.

This second monitoring data, of a lower design assurance level, is transmitted to the second receiving interface 52.

At any time, the first evaluation module 70 receives exclusively the first data from the first interface 50, and implements, for each monitored pilot state, the deterministic algorithm present in the first state machine 80 corresponding to the monitored pilot state.

For each monitored pilot state, the implementation of the algorithm, based on the first data, leads to the determination of a high-level pilot state, which can be a high-level normal state or a high-level degraded state.

Simultaneously, in an activation configuration, the second lower level evaluation module 72 receives the second data from the second interface 52, optionally accompanied by first data from the first interface 50.

For each monitored pilot state, it then implements the deterministic algorithm of the second state machine 82.

The second state machine 82 is thus able to produce, for each monitored pilot state, a low-level pilot state, which may be a normal low-level state, or a degraded low-level state.

The consolidation module 74 then receives, for each monitored pilot state, the high-level pilot state and the low-level pilot state and determines a consolidated pilot state.

If both the high level and low-level pilot states are normal states, the consolidation module 74 determines that the consolidated pilot state is a normal state.

If instead one or fewer of the low-level or high-level pilot states is a degraded state, the consolidation module 74 determines that the consolidated pilot state is a degraded state.

Each pilot state assigned by the consolidation module 74 is then transmitted to the display manager 58 to generate and display the monitoring window 90 with the or each pilot state determined at the given time.

Furthermore, each pilot state is also transmitted to the information and/or alarm generator 60. In the event of a degraded pilot state, the information and/or alarm generator 60 first activates the display manager 58 to generate and display the pilot prompting window 100, and then in the absence of pilot response to this window 100, activates the alarms defined above.

If the pilot feels that the generated alarm is unjustified or is a nuisance, they activate the parameter setting window 99. They can then test the correct operation of the detection sensors 28 or the camera system 30 using the buttons 102. Alternatively, the operator may activate the command 76 to disable the second lower level evaluation module 72 and prevent a low-level pilot state from being transmitted to the consolidation module 74. The consolidation module 74 then determines the pilot state solely on the basis of the high-level pilot state.

The monitoring system 10 according to the present disclosure therefore very reliably detects via the first high-level evaluation module 70, within a certain time period (e.g. a typical duration of about 5 minutes), that a pilot on duty is absent from their station or is incapacitated or in deep sleep. This maximum delay is reduced by the presence of the lower-level evaluation module 72, which detects degraded pilot states much more sensitively, even though the sensors that are used for this detection are of a lower design assurance level.

Thus, by segregating the data received by the pilot determination unit 54 between the first data of a high design assurance level, and the second data of a lower design assurance level, the dual objectives of safety and responsiveness of the monitoring system 10 can be met.

The monitoring system 10 according to the present disclosure has a very high level of security thanks to the segregation into two levels of detection, one reliable but of reduced performance, and a more responsive but potentially harmful or disruptive one, and the ability to isolate this second level.

The monitoring system 10 according to the present disclosure is furthermore responsive, since the second lower-level evaluation module 72 receives richer data than that used by the first evaluation module 70, allowing for a finer detection of degraded states and often faster.

In any case, even if the second lower-level data is of a lower design assurance level than the first higher-level data, it can be automatically excluded by the lower-level evaluation module 72 when a sensor that produces this data is detected as non-operational. They can also be voluntarily overridden by the pilot, who can use the command 76 to disable consideration of the low-level pilot state.

Thus, the monitoring system 10 is reliable enough to be certifiable, yet responsive enough to be operational for pilots when everything is working nominally, which is the usual situation.

The monitoring system 10 is able to operate in a degraded manner by selecting the remaining available sensors, while providing the user with the ability to disregard the data produced by the low design assurance level sensors if they give erroneous results.

In addition, the monitoring system 10 allows the integration of data from enhanced design assurance level sensors, for example enhanced seat sensors, into the high level design monitoring data via the interface 50. It also allows for new sensors to be taken into account in addition to the detection sensor 28 and the camera system 30, even if they are less reliable.

Similarly, the monitoring system 10 may use data from the lower design level avionics bus 19 that is retrieved by the second interface 52.

In one embodiment (not shown), the algorithm implemented by the second lower level evaluation module 72 is not a deterministic algorithm, but is for example an algorithm that operates by learning. The algorithm implemented by the first high-level evaluation module 70 remains a deterministic algorithm.

In another embodiment, the consolidated pilot state obtained for the or each determined pilot state is suitable for switching from a normal state to a plurality of degraded states of different levels.

What is claimed is:

1. An aircraft crew operational state monitoring system comprising:
   a first interface configured to receive first crew monitoring data, the first crew monitoring data having a high design assurance level;
   a second interface configured to receive second crew monitoring data, the second crew monitoring data having a lower design assurance level than the first crew monitoring data; and
   a pilot state determiner configured to determine at least one monitored pilot state based on the high design assurance level first crew monitoring data received from the first receiving interface, and based on the lower design assurance level second crew monitoring data received from the second receiving interface,
   for the at least one monitored pilot state, the pilot state determiner being configured to implement a first deterministic algorithm to obtain a high-level pilot state from the high design assurance level first crew monitoring data, regardless of the lower design assurance level second crew monitoring data;
   the pilot state determiner being configured to determine a low-level pilot state, from at least the lower design assurance level second crew monitoring data;
   the pilot state determiner being configured to determine a consolidated pilot state, the consolidated pilot state being obtained in an active configuration of the low-level pilot state determination as a function of the high-level pilot state and of the low-level pilot state, and is obtained in an inactive configuration of the low-level pilot state determination as a function of the high-level pilot state, without taking the low-level pilot state into account.

2. The system according to claim 1, wherein the consolidated pilot state determined by the pilot state determiner is configured to change from a normal state to at least one degraded state, the high-level pilot state being configured to change from a normal high-level state to at least one degraded high-level state, the low-level pilot state being configured to change from a normal low-level state to a degraded low-level state, the pilot state determiner being configured to establish a degraded pilot state when a high-level degraded pilot state and/or when a low-level degraded pilot state are determined.

3. The system according to claim 1, wherein pilot state determiner comprises a first finite-state machine implementing the first deterministic algorithm.

4. The system according to claim 1, wherein the pilot state determiner is configured to implement a second deterministic algorithm to determine the low-level pilot state.

5. The system according to claim 4, wherein the pilot state determiner comprises a second finite-state machine implementing the second deterministic algorithm.

6. The system according to claim 1, wherein the first receiving interface is configured to receive, together with each item of first crew monitoring data, a first validity level associated with the first crew monitoring data item, the second receiving interface being configured to receive, together with each item of second crew monitoring data, a second validity level associated with the second crew monitoring data item, the pilot state determiner being configured to take into account the first and second validity levels of the first crew monitoring data item and of the second crew monitoring data item in order to determine the high-level and low-level pilot states and/or to determine a pilot state validity level.

7. The system according to claim 1, wherein the pilot state determiner is configured to obtain the low-level pilot state based on the lower design assurance level second crew monitoring data obtained from the second interface and on the high design assurance level first crew monitoring data obtained from the first interface.

8. The system according to claim 1, wherein the pilot state determiner is configured to calculate a high level confidence level associated with the obtained high-level pilot state, the pilot state determiner being configured to calculate a low level confidence level associated with the obtained low-level pilot state, the pilot state determiner being configured to calculate a consolidated confidence level associated with the consolidated pilot state, based on the high-level confidence level and on the low-level confidence level.

9. The system according to claim 1, wherein the consolidated pilot state is selected from a state of presence at an aircraft crew work station, a state of aircraft operation ability, a state of incapacitation and/or of sleep, a state of alertness, a state of drowsiness, distraction and/or inattention, a state of work overload, a state of mental overload, a state of stress, a state of present situation awareness, a state of task engagement, a state of physical activity level, and/or a state of pilot activity consistency and relevance with the mission.

10. The system according to claim 1, wherein the pilot state determiner comprises a lower-level state determination deactivation command accessible to a crew member, the lower-level state determination deactivation command being operable to switch the pilot state determiner from the active configuration of the low-level pilot state determination to the inactive configuration of the low-level pilot state determination.

11. The system according to claim 1, wherein the first receiving interface and/or the second receiving interface is configured to receive first crew monitoring data and/or second crew monitoring data from an avionics system and/or from a crew member's interaction with a human/machine interface of the avionics system.

12. The system according to claim 1, wherein the first receiving interface and/or the second receiving interface is configured to receive first crew monitoring data and/or second crew monitoring data from at least one crew member state monitoring sensor.

13. The system according to claim 12, wherein the at least one crew member state monitoring sensor comprise a crew member seat presence sensor, an optical detection sensor with a field of view facing a seat of the crew member, a camera operating in the visible, near-infrared, or thermal spectrum, and/or a 2D and/or 3D time-of-flight camera, and/or crew physiological parameters detecting sensor, an ECG sensor, a breathing detection sensor, an EEG sensor, an FNIR sensor, a connected watch, a connected bracelet or a connected garment.

14. The system according to claim 1, further comprising a display and a display manager on the display, the display manager being configured to generate and display on the display a status monitoring window illustrative of the consolidated pilot state determined by the pilot state determiner.

15. The system according to claim 1, further comprising an information generator, and/or an alarm generator configured to generate at least one item of information, and/or at least one alarm when the consolidated pilot state determined by the pilot state determiner is in a degraded state.

16. An aircraft crew operational state monitoring method, implemented in an aircraft crew operational state monitoring system, comprising:

receiving, via a first receiving interface of the monitoring system, first crew monitoring data, the first crew monitoring data having a high design assurance level;

receiving, via a second receiving interface of the monitoring system, second crew monitoring data having a lower design assurance level than the first crew monitoring data;

determining, via a pilot state determiner of the monitoring system, at least one pilot state based on the high design assurance level first crew monitoring data received from the first receiving interface, and based on the lower design assurance level second crew monitoring data received from the second receiving interface, the at least one pilot state determining comprising, for the at least one monitored pilot state:

implementing a deterministic algorithm via the pilot state determiner to obtain a high-level pilot state from the high design assurance level first crew monitoring data, regardless of the lower design assurance level second crew monitoring data;

determining a low-level pilot state via the pilot state determiner from at least the lower design assurance level second crew monitoring data;

determining a consolidated pilot state via the pilot state determiner, the consolidated pilot state being obtained in an active configuration of the low-level pilot state determining as a function of the high-level pilot state and the low-level pilot state, and being obtained in an inactive configuration of the low-level pilot state determining as a function of the high-level pilot state, without taking the low-level pilot state into account.

17. The method according to claim 16, wherein when the high-level pilot state changes from a normal high-level state to a degraded high-level state, and/or when the low-level pilot state corresponding to the high-level pilot state changes from a normal low-level state to a degraded low-level state, the method comprising changing the consolidated pilot state from a normal state to a degraded state.

\* \* \* \* \*